(12) United States Patent
Brusasco et al.

(10) Patent No.: US 8,716,663 B2
(45) Date of Patent: May 6, 2014

(54) DEVICE AND METHOD FOR PARTICLE THERAPY MONITORING AND VERIFICATION

(75) Inventors: Caterina Brusasco, Bossiere (BE); Bruno Marchand, Mont-Saint-Guibert (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 293 days.

(21) Appl. No.: 12/991,372

(22) PCT Filed: May 6, 2009

(86) PCT No.: PCT/EP2009/055484
§ 371 (c)(1),
(2), (4) Date: Jun. 28, 2011

(87) PCT Pub. No.: WO2009/135879
PCT Pub. Date: Nov. 12, 2009

(65) Prior Publication Data
US 2011/0248188 A1    Oct. 13, 2011

(30) Foreign Application Priority Data
May 6, 2008    (EP) .................................. 08155747

(51) Int. Cl.
*G01T 1/00*    (2006.01)
(52) U.S. Cl.
USPC ...................................................... 250/336.1
(58) Field of Classification Search
USPC ...................................................... 250/336.1
See application file for complete search history.

(56) References Cited

U.S. PATENT DOCUMENTS

| | | | |
|---|---|---|---|
| 6,661,870 B2 | 12/2003 | Kapatoes et al. | |
| 6,677,597 B1 | 1/2004 | Haberer et al. | |
| 6,853,702 B2 | 2/2005 | Renner | |
| 7,856,082 B2 | 12/2010 | Flynn et al. | |
| 7,907,987 B2 | 3/2011 | Dempsey | |
| 2007/0034812 A1* | 2/2007 | Ma et al. | 250/492.21 |
| 2009/0116616 A1 | 5/2009 | Lu et al. | |
| 2010/0054413 A1 | 3/2010 | Sobering et al. | |
| 2012/0108958 A1* | 5/2012 | Jackson | 600/427 |

FOREIGN PATENT DOCUMENTS

| | | |
|---|---|---|
| JP | 2002522127 A | 7/2002 |
| JP | 2007526036 A | 9/2007 |
| WO | 00/07667 A1 | 2/2000 |

(Continued)

OTHER PUBLICATIONS

Extended European Search Report, European Patent Application No. 08155747.2, dated Oct. 27, 2008, 5 pages.

(Continued)

*Primary Examiner* — David Porta
*Assistant Examiner* — Hugh H Maupin
(74) *Attorney, Agent, or Firm* — Fitch, Even, Tabin & Flannery LLP

(57) ABSTRACT

The present invention relates to a device and method for monitoring and verification of the quality of a radiation treatment beam in conformal radiation therapy, and in particular for IMPT (Intensity Modulated Particle Therapy) applications. The device comprises a 2D electronic detector measuring 2D responses to the delivered treatment beam. These 2D responses are compared with predicted 2D responses and differences in responses are signalled. Based on the measured 2D responses the effectively delivered 3D dose distribution in the target can be reconstructed.

19 Claims, 8 Drawing Sheets

(56) References Cited

FOREIGN PATENT DOCUMENTS

| WO | WO0007667 A1 | 2/2000 |
| --- | --- | --- |
| WO | 03/092813 A1 | 11/2003 |
| WO | 03/101538 A1 | 12/2003 |
| WO | WO2005081842 A2 | 9/2005 |
| WO | 2007/012147 A2 | 2/2007 |
| WO | 2008/006198 A1 | 1/2008 |
| WO | 2008/053026 A1 | 5/2008 |

OTHER PUBLICATIONS

Examination Report, European Patent Application No. 09 742 097.0, dated Mar. 6, 2012, 3 pages.

Anders Ahnesjö, "Collapsed Cone Convolution of Radiant Energy for Photon Calculation in Heterogeneous Media," Med. Phys. 16(4), 1989, pp. 577-592, 16 pages.

Bonin et al, "A Pixel Chamber to Monitor the Beam Performances in Hadron Therapy," Nuclear Instruments and Methods in Physics Research, A 519 (2004), pp. 674-686, 13 pages.

Brusasco et al, "A Dosimetry System for Fast Measurement of 3D Depth-Dose Profiles in Charged-Particle Tumor Therapy with Scanning Techniques," Nucl. Instr. Meth. In. Phys. Res. B 168(4), Aug. 2000, pp. 578-592, 15 pages.

Frelin et al, "The DosiMap, a New 2D Scintillating Dosimeter for IMRT Quality Assurance: Characterization of Two Cerenkov Discrimination Methods," Med. Phys. vol. 35, No. 5, (2008), pp. 1651-1662, 12 pages.

Gottschalk and R. Platais, "Nuclear Interactions of 160 MeV Protons Stopping in Copper: A Test of Monte Carlo Nuclear Models," Med. Phys. 26(12), Dec. 1999, pp. 2597-2601, 5 pages.

Kapatoes et al, "A Feasible Method for Clinical Delivery Verification and Dose Reconstruction in Tomotherapy," Med. Phys, vol. 28(4), Apr. 2001, pp. 528-542, 15 pages.

Kapatoes et al, "Delivery Verification in Sequential and Helical Tomotherapy," Phys. Med. Biol, vol. 44, Jan. 1999, pp. 1815-1841, 27 pages.

Kapatoes et al, "On the Accuracy and Effectiveness of Dose Reconstruction for Tomotherapy," Phys. Med. Biol, vol. 46, Jan. 2001, pp. 943-966, 24 pages.

Kimstrand et al., "A Beam Source Model for Scanned Proton Beams." Phys. Med. Biol., vol. 52, 2007, pp. 3151-3168, 18 pages.

Lomax et al, "Intensity Modulation Methods for Proton Radiotherapy," Phys. Med. Biol. 44 (1999), pp. 185-205, 21 pages.

Lomax et al, "Treatment Planning and Verification of Proton Therapy Using Spot Scanning: Initial Experiences," Med. Phys. 31 (11), Nov. 2004, pp. 3150-3157, 8 pages.

Low et al, "A Technique for the Quantitative Evaluation of Dose Distributions," Med. Phys. 25(5), May 1998, pp. 656-661, 6 pages.

Nikos Papanikolaou, "Investigation of the Convolution Method for Polyenergetic Spectra," Med. Phys. 20 (5), 1993, pp. 1327-1336, 10 pages.

Pedroni et al., "Experimental Characterization and Physical Modelling of the Dose Distribution of Scanned Proton Pencil Beams." Phys. Med. Biol., vol, 50, 2005, pp. 541-561, 21 pages.

Timmer et al, "A Scintillating GEM for 2D-Dosimetry in Radiation Therapy," Nucl. Instr. and Methods in Physics Research Section A, vol. 478, (2002), pp. 98-103, 6 pages.

Wolfgang A. Tomé, "Beam Modeling for a Convolution/Superposition-Based Treatment Planning System," Medical Dosimetry, vol. 27, No. 1, 2002, pp. 11-19, 9 pages.

Yong Yang, "A Three-Source Model for the Calculation of Head Scatter Factors," Med. Phys. 29(9), 2002, pp. 2024-2033, 10 pages.

International Search Report, International Application No. PCT/EP2009/055484, date of completion of the report Jul. 24, 2009, 3 pages.

International Search Report, International Application No. PCT/EP2009/055488, date of completion of the report Jul. 16, 2009, 4 pages. (corresponds to U.S. Appl. No. 12/991,386).

International Preliminary Report on Patentability With Written Opinion, International Application No. PCT/EP2009/055484, date of issuance of this report Nov. 9, 2010, 5 pages.

International Preliminary Report on Patentability With Written Opinion, International Application No. PCT/EP2009/055488, date of issuance of this report Nov. 9, 2010, 8 pages. (corresponds to U.S. Appl. No. 12/991,386).

\* cited by examiner

DEVICE AND METHOD FOR PARTICLE THERAPY MONITORING AND VERIFICATION

CROSS REFERENCE TO RELATED APPLICATIONS

This application is a national phase application of International Application No. PCT/EP2009/055484, filed May 6, 2009, designating the United States and claiming priority to European Patent Application No. 08155747.2, filed May 6, 2008, both of which are incorporated by reference herein in their entirety.

FIELD OF THE INVENTION

The present invention relates generally to particle radiation therapy monitoring and verification. More particularly, the present invention relates to a method and device for quality assurance in particle therapy, i.e. ensuring that the particle radiation doses delivered in an object correspond to what is planned.

STATE OF THE ART

Radiotherapy using particles has proven to be a precise and conformal radiation therapy technique where a high dose to a target volume can be delivered while minimizing the dose to surrounding healthy tissues. A particle radiation apparatus comprises an accelerator producing energetic charged particles, a beam transport system and a particle beam delivery system. The particle beam delivery system is responsible to deliver a conformal dose distribution to the target volume and monitor and measure the dose delivered. Various types of particle beam delivery systems exist, applying different techniques to deliver a conformal dose to the target volume. There are two major techniques used in particle beam delivery: the more common passive scattering techniques and the more sophisticated dynamic radiation techniques.

An example of a dynamic technique is the so-called pencil beam scanning (PBS) technique. In PBS a narrow particle pencil beam is magnetically scanned on the plane orthogonal to the central beam direction. Lateral conformity in the target volume is obtained by adequate control of the scanning magnets. By varying the energy of the particle beam, different layers in the target volume, characterized by their fixed particle energy, can subsequently be irradiated. In this way, particle radiation dose can be delivered to the entire 3D target volume.

The sum of all layer irradiations delivered to the target volume, while keeping the same beam-to-object geometry, is called a treatment beam or a treatment field. When using a particle radiation treatment apparatus comprising a gantry device various treatment beams can be delivered to the target volume from different gantry angles. Alternatively, the beam-to-object geometry can also be modified by rotation of the object with respect to the beam. The sum of all treatment beams to be delivered during the same irradiation session is defining a treatment fraction. The geometry and characteristics of the treatment beams to be delivered by the particle radiation apparatus during a fraction are specified in a treatment plan. Prior to irradiation the particle radiation apparatus receives the treatment plan from the treatment planning system, specifying the characteristics of the treatment beams to be delivered. The particle radiation apparatus is configurable for delivery of treatment beams based on a given set of treatment beam parameters specified in the treatment plan.

Multiple variations of pencil beam scanning techniques exist. There is the so-called spot scanning technique where the layer irradiation is performed by delivering a prescribed particle dose at discrete spot positions in the target volume and by interrupting the beam inbetween spot positions. Another method is the continuous scanning technique where the beam spot is continuously scanned following a predefined scanning pattern. During the scanning of a layer, the particle intensity can be varied instant by instant in order to deliver the right particle radiation dose at the right place in the target volume, as specified in the treatment plan. In more advanced beam delivery systems also the scanning speed can be adjusted instant by instant in order to have an additional degree of freedom to modulate the particle intensity. Other variations of scanning techniques have been proposed. For example a scanning technique where at each spot position the particle energy is varied to cover the target region in depth before going to the next spot position. An even more advanced technique is a technique where both spot position and particle energy are varied together.

With the PBS technique, not only homogenous dose distributions can be delivered to the target volume but also inhomogenous dose distributions can be delivered as specified with advanced treatment planning systems. Typically, a combination of several treatment beams coming from different beam directions (e.g. by selecting another gantry angle or by rotating the object with respect to the beam direction) is needed to produce a custom tailored radiation dose that optimises the dose in the target volume while also protecting adjacent normal tissues. As a result, the 3-D dose distribution in the target volume resulting from one single treatment beam direction might not be uniform, it is uniform when the integral of the dose contributions from all treatment beams of the treatment fraction are delivered. The delivery of inhomogenous treatment beams which add up to a homogenous and conformal dose in the target volume is called Intensity Modulated Particle Therapy (IMPT). The specification of the treatment beams is performed by advanced treatment planning systems using optimization algorithms to specify the number and directions of treatment beams and the particle intensities to be delivered for each spot position in each layer of each treatment beam.

Another example of a dynamic particle radiation technique that differs from pencil beam scanning is the so called wobbling technique, also named uniform scanning technique, where a uniform dose is delivered to a target volume layer per layer and the beam is continuously scanned over a fixed geometrical scanning pattern. In this method the beam does not follow the contour of the target volume but the beam is scanned within a predefined geometrical area (square, rectangle, circle, . . . ) and lateral conformity is accomplished by using a multileaf collimator or a patient specific aperture.

The present invention is related to treatment beam verification and QA measurements and is applicable for any type of particle radiation technique and is not limited to the techniques described above. The invention is however of particular interest for the more complex dynamic particle delivery systems and especially when IMPT is applied. The efficiency of radiation therapy relies on the accuracy of dose delivery, and, as a result, quality assurance procedures are of critical importance to detect any possible error in the chain of operations that from treatment planning leads to the treatment delivery. Because of the large number of time-variable parameters to be controlled by the delivery machine during the irradiation of the treatment, IMPT places even more stringent demands on these verification procedures, and makes them even more essential. The non-homogeneity of the dose distributions in IMPT fields make single point-dose measurements inadequate in verifying the correct dose delivery.

General quality assurance measurements and specific treatment beam verification measurements for particle therapy radiation systems are in general performed by measuring 3D dose distributions in a phantom. Lomax et al, "Treatment planning and verification of proton therapy using spot scanning: initial experiences", Med. Phys. 31 (11), November 2004, discloses a method for treatment beam specific QA verification comprising the steps of for each treatment beam dose distribution in the object, calculating the waterequivalent 3D dose distribution in water using the treatment planning system, measuring two orthogonal profiles using an ionization chamber array consisting of two arms of thirteen ionization chambers each, repeating the measurement at various depths in water, using the planning system to compare the measured values with predicted values. Brusasco et al, "A dosimetry system for fast measurement of 3D depth-dose profiles in charged-particle tumor therapy with scanning techniques", Nucl. Instr. Meth. In Phys. Res. B 168 (2000) 578-592, discloses a system to perform treatment beam verifications with a detector system comprising a position sensitive detector with a stack of ionization chambers and range-shifter.

The current techniques applied for treatment verification and quality assurance are time consuming and too cumbersome for day-to-day routine. Moreover the treatment verifications are only performed once and one can not guarantee that performances of the particle radiation apparatus at the day of the verification measurements in a phantom are the same as on the day of treatment beam delivery to the object. Differences in the daily treatment beam characteristics from day to day can result in differences in the final 3D dose distribution in the object when compared to the initially planned 3D dose distribution. The complexity of the IMPT treatments makes it also difficult for the operators to detect possible deviations from the planned sequence of irradiations during the delivery of the various treatment beams and layers.

Therefore, there is a need for a device, independent from the particle radiation apparatus and independent from the treatment planning system, for monitoring and verifying the treatment beams during irradiation of the object and without interfering with the delivery process. The device should be capable of signalling errors with respect to the treatment beam delivery to allow the operator to interact and take adequate decisions about the continuation of the beam delivery. In addition there is a need to know the actual delivered 3D dose distribution to the object based on the actual treatment beam characteristics at the day of beam delivery.

Patent application WO 03/101538A1 discloses a particle radiation apparatus for irradiating a target volume using a scanning technique for scanning the beam in an X,Y plane perpendicular to the beam direction. This radiation apparatus (R-APP) is shown on FIG. 1A. This R-APP comprises a reference generator for calculating the trajectories of the beam (comprising scanning speed in x and y, beam current, required positions $x(t), y(t)$), a monitor system to determine the actual positions $x(t), y(t)$ of the beam as function of time, an outer control loop for comparing the required positions $x(t), y(t)$ with the actual positions $x(t), y(t)$ and for applying corrections to the positions by adjusting the scanning speed in x and y. This radiation apparatus disclosed in WO 03/101538A1 receives as an input a dose map from a treatment planning system (TPS). With the outer loop verification system as disclosed the actual beam positions are compared with calculated beam positions by the reference generator which is a component of the radiation apparatus R-APP. With this system the instantaneous positions x and y are measured and verified as function of time. This system does not verify that resulting overall dose distribution in the target corresponds to the required dose distribution as specified by the TPS, it only verifies that the beam instantaneous trajectories (defined through machine settings, e.g. x,y positions) calculated by an internal component of the R-APP are correct. Also for example potential errors in the downloading process from TPS to R-APP are not detected.

AIMS OF THE INVENTION

The present invention aims to provide an independent device and method to perform treatment beam verifications delivered with a particle radiation apparatus that do not present the drawbacks of the state of the art.

In particular, the present invention aims to reduce the extended, time consuming QA and treatment plan verifications needed for dynamic particle therapy systems.

The present invention aims also to provide a device for detecting or signalling errors during delivery of a treatment beam independently of the monitor system of the particle treatment beam apparatus.

Furthermore, the present invention aims to considerably enhance the state of the art methods of patient plan verification, by allowing computation and verification of the delivered 3D dose distributions in the object based on measured treatment beam data.

SUMMARY OF THE INVENTION

The present invention is related to a device as described in the appended claims.

According to a first aspect of the present invention a device for monitoring and verification of treatment beam delivery with a particle radiation apparatus is described. The treatment beam comprises one or more treatment beam layers characterized by a set of treatment beam layer parameters. A treatment beam layer comprises particles having essentially the same energy. The particle radiation apparatus is configurable for a given set of treatment beam layer parameters. The device according to the invention comprises:

- means to receive treatment beam layer parameters for each said treatment beam layer of each said treatment beam;
- an electronic 2D detector device capable of measuring 2D responses of said treatment beam layer in a plane perpendicular to the central axis of said treatment beam;
- a 2D detector response predicting module determining the predicted 2D detector responses for each said treatment beam layer to be delivered with said particle radiation apparatus configured with said set of treatment beam layer parameters;
- a memory to store the predicted 2D detector responses of each said treatment beam layer;
- means to acquire in real time the 2D detector responses caused by a treatment beam layer delivered by said particle radiation apparatus being configured with said set of treatment beam layer parameters;
- a 2D detector response comparison module performing a comparison between the measured 2D detector responses and the corresponding said predicted 2D detector responses;
- an error handling module signalling difference between said measured 2D detector responses and said predicted 2D detector responses.

The particles of the radiation apparatus are typically charged hadrons such as protons, alpha particles, carbon ions.

The particles of a specific layer are forming a particle sub beam. Remark that in practice the energy of such a particle sub beam is not mono-energetic but the beam has a certain energy spread. The energy spread of the beam can be influenced by several components of the radiation apparatus (e.g. accelerator, energy adjusting devices, any material in the beam line and beam delivery system such as monitor detectors, . . . ).

In general, rather than characterising a particle beam by its energy one characterises a particle beam by its water-equivalent penetration depth or range expressed in $g/cm^2$. The nominal range of a particle beam or Bragg peak is then defined as the range where the Bragg peak dose intensity drops below a given value (e.g. 90% or 80% range value). When a layer is characterized by an energy, this has to be interpreted as the energy corresponding to the 80% or 90% maximum penetration depth (other definitions for defining the range can be used as well).

Remark that in some cases ridge filters are used to reduce the number of layers. By using a ridge filter the energy of the particles is spread out in order to obtain a so-called Spread-Out-Bragg peak. Instead of using a ridge filter, other means to spread out the Bragg peak can be applied as well. The definition of the maximum range of a layer defined above can still be applied when a ridge filter is used and hence the concept of specifying treatment beam layer parameters on the level of the treatment planning is still valid in the context of using ridge filters.

According to the first aspect of the present invention, the prediction of the 2D detector responses is performed with the 2D detector response predicting module. This module comprises:
  a 2D detector fluence calculation device calculating the particle fluence at the 2D detector position for said treatment beam layer parameters; said particle fluence calculation device comprising a beam model, said beam model being based on a set of beam model parameters, said beam model parameters comprising characteristics of the said particle radiation apparatus and said particles;
  a 2D detector response calculation device calculating for a given said particle fluence at the 2D detector position the corresponding 2D detector responses, said 2D detector response calculation device comprising a detector model of said 2D detector system describing the geometry of the 2D detector and a detector response model describing the response of the 2D detector to particle irradiation;

Preferably, in another embodiment of the device, the said 2D detector fluence calculation device and/or the said 2D detector response calculation device is based on a Monte Carlo algorithm calculating the particle fluence at the 2D detector position and/or calculating the 2D detector responses.

Preferably, in the preferred embodiment, the device comprises means to measure the energy of the particles of a treatment beam layer. The particle energy can be determined by various means. In a preferred embodiment of the invention, the device comprises a particle range detector, said particle range detector comprising means to measure the particle waterequivalent range, said particle waterequivalent range being function of said particle energy. In another embodiment, the device comprises an energy calculating device, said energy calculating device being examining distortions in the shape of the measured 2D detector responses when compared with the said predicted 2D detector responses, said distortions being function of variations in said energy.

The device according to the invention can perform a comparison between the said measured energy of a treatment beam layer and the prescribed layer energy and signal the difference in energy and/or signal an error when the comparison is out of predefined limits.

Preferably, the device according to the first aspect of the present invention further comprises:
  means to import a description or image of an object, said description or image comprising the 3D shape, density distribution and position of the target volume and/or organs at risk within the object;
  a treatment beam parameters reconstructing device capable of computing for each delivered treatment beam layer the delivered treatment beam layer parameters based on the said measured 2D detector responses of each layer and a beam model, said beam model being characterized by a set of beam model parameters;
  a particle fluence calculation device calculating for each delivered treatment beam layer the delivered layer particle fluence through the object based on the said delivered treatment beam layer parameters and said beam model;
  a dose calculation device capable of computing the delivered 3D dose distribution within the said object, said 3D dose distribution resulting from one or more delivered treatment beams, each said delivered treatment beam comprising one or more said delivered treatment beam layers, said computing the delivered 3D dose distribution being based on said delivered layer particle fluence of each layer of each treatment beam;
  means to visualize the said delivered 3D dose distribution in the object.

Alternatively, the said particle fluence calculation device and/or said dose calculation device is based on a Monte Carlo algorithm for calculating the delivered particle layer fluences and/or 3D dose distributions.

Preferably, the said particle fluence calculation device and/or said dose calculation device are using the said measured energy as an input parameter for the calculations. The measured energy is obtained from either the said range detector or it is obtained with the said energy calculating device based on the 2D detector responses.

Preferably, the said treatment beam parameter reconstructing device further comprises an iterative algorithm updating the said beam model parameters and/or said layer treatment beam parameters until the comparison between the measured 2D detector responses and the corresponding predicted 2D detector responses minimizes a scoring function and assigning the new values of beam model and/or treatment beam layer parameters, obtained after minimizing the scoring function, as the delivered beam model parameters and/or delivered treatment beam layer parameters. The particle fluence calculation device calculating the particle fluence through the object is then using the said delivered treatment beam layer parameters and the said delivered beam model parameters.

Advantageously, the device can make a comparison between the planned 3D dose distribution from an external planning system and the said delivered 3D dose distribution. To perform this comparison the device comprises:
  means to import the planned 3D dose distribution in the object as calculated by an external treatment planning system;
  means to compare the said planned 3D dose distribution with the said delivered 3D dose;
  means to report a set of parameters resulting from said comparison.

More advantageously, the device further comprises means to:
- store the said delivered 3D dose distribution delivered during a treatment fraction;
- accumulate the delivered 3D dose distributions delivered during subsequent treatment fractions;
- visualize the accumulated 3D dose distribution in the object.

More advantageously, the device further comprises means to:
- acquire an updated description or image of an object;
- store the updated description or image of the object;
- visualize the accumulated 3D dose distribution with the said updated description or image of the object.

Preferably, the device further comprises an input module for importing a treatment plan from an external device, said treatment plan comprising a plurality of parameters, said plurality of parameters comprising said treatment beam layer parameters, said a description or image of an object, said planned 3D dose distribution.

Preferably, the device according to the first aspect of the present invention is capable of operating independently from the particle radiation apparatus, receiving only a treatment plan from an external device and optionally receiving synchronisation signals from a particle radiation apparatus for synchronising the 2D detector device with the treatment beam delivery. Said external device can be a Treatment planning system (TPS).

Preferably, the device further comprises a commissioning module to optimise said set of beam model parameters based on measured data with the said particle radiation apparatus.

According to a second aspect of the present invention a method for verifying treatment beam delivery with a particle radiation apparatus prior to patient irradiation is described. The method comprising the steps of:
- providing a particle radiation apparatus for delivery of a said treatment beam, said treatment beam comprising one or more treatment beam layers, said treatment beam layer being characterized by a set of treatment beam layer parameters, said treatment beam layer comprising particles having the same energy, said particle radiation apparatus being configurable for a given said set of treatment beam layer parameters;
- providing means to receiving prescribed treatment beam layer parameters;
- providing a 2D detector system capable of providing a measured 2D detector response of said treatment beam layer in a plane perpendicular to the central axis of said treatment beam;
- For each layer of said plurality of layers:
  - determining a predicted 2D detector response for said prescribed treatment beam layer parameters;
  - delivering said treatment beam layer with said particle radiation apparatus being configured with said prescribed treatment beam layer parameters;
  - measuring the 2D detector responses caused by the treatment beam layer delivered by said particle radiation apparatus;
  - performing a comparison between the measured 2D detector response and the corresponding predicted 2D detector response;
  - signalling difference between said measured 2D detector response and said predicted 2D detector response.

Preferably, the method further comprises steps of:
- providing means to determine the layer energy of a said treatment beam layer;
- For each layer of said plurality of layers:
  - determining the delivered layer energy of the particles;
  - performing a comparison between the said delivered layer energy and the prescribed layer energy, the prescribed layer energy being comprised by the layer treatment beam parameters;
  - signalling difference between said measured layer energy and said prescribed layer energy.

Preferably, the method further comprises the steps of:
- providing a description of an object, said description, which can be an image, comprising the 3D shape, density distribution and position of the target volume within the object;
- computing for each delivered treatment beam layer the corresponding delivered treatment beam layer parameters based on the said measured 2D detector responses of each layer and a beam model, said beam model being characterized by a set of beam model parameters;
- computing for each delivered treatment beam layer the delivered layer particle fluence through the object based on the said delivered treatment beam layer parameters and said beam model;
- computing the delivered 3D dose distribution within the said object, said 3D dose distribution resulting from one or more delivered treatment beams, each said delivered treatment beam comprising one or more said delivered treatment beam layers, said computing the delivered 3D dose distribution is based on said delivered layer particle fluence of each layer of each treatment beam;
- visualizing the said delivered 3D dose distribution in the object.

Preferably:
the step of said computing delivered treatment beam layer parameters comprises the steps of:
  a. providing new values for said treatment beam layer parameters and/or said beam model parameters;
  b. obtaining new predicted 2D detector responses based on new values for said treatment beam layer parameters and/or beam model parameters;
  c. repeating steps a and b until the comparison between the measured 2D detector responses and the corresponding predicted 2D detector responses minimizes a scoring function;
  d. assigning the new values of treatment beam layer parameters and/or beam model parameters obtained after minimizing the scoring function as the said delivered treatment beam layer parameters and/or delivered beam model parameters.

said step of computing for each delivered treatment beam layer the delivered layer particle fluence through the object being based on the said delivered treatment beam layer parameters and said delivered beam model parameters.

Advantageously, the method further comprises the steps of:
- importing the planned 3D dose distribution in the object as calculated by an external treatment planning system;
- comparing the said planned 3D dose distribution with the said delivered 3D dose;
- reporting a set of parameters resulting from said comparison.

DETAILED DESCRIPTION OF PREFERRED EMBODIMENTS OF THE PRESENT INVENTION

Figure 1A:
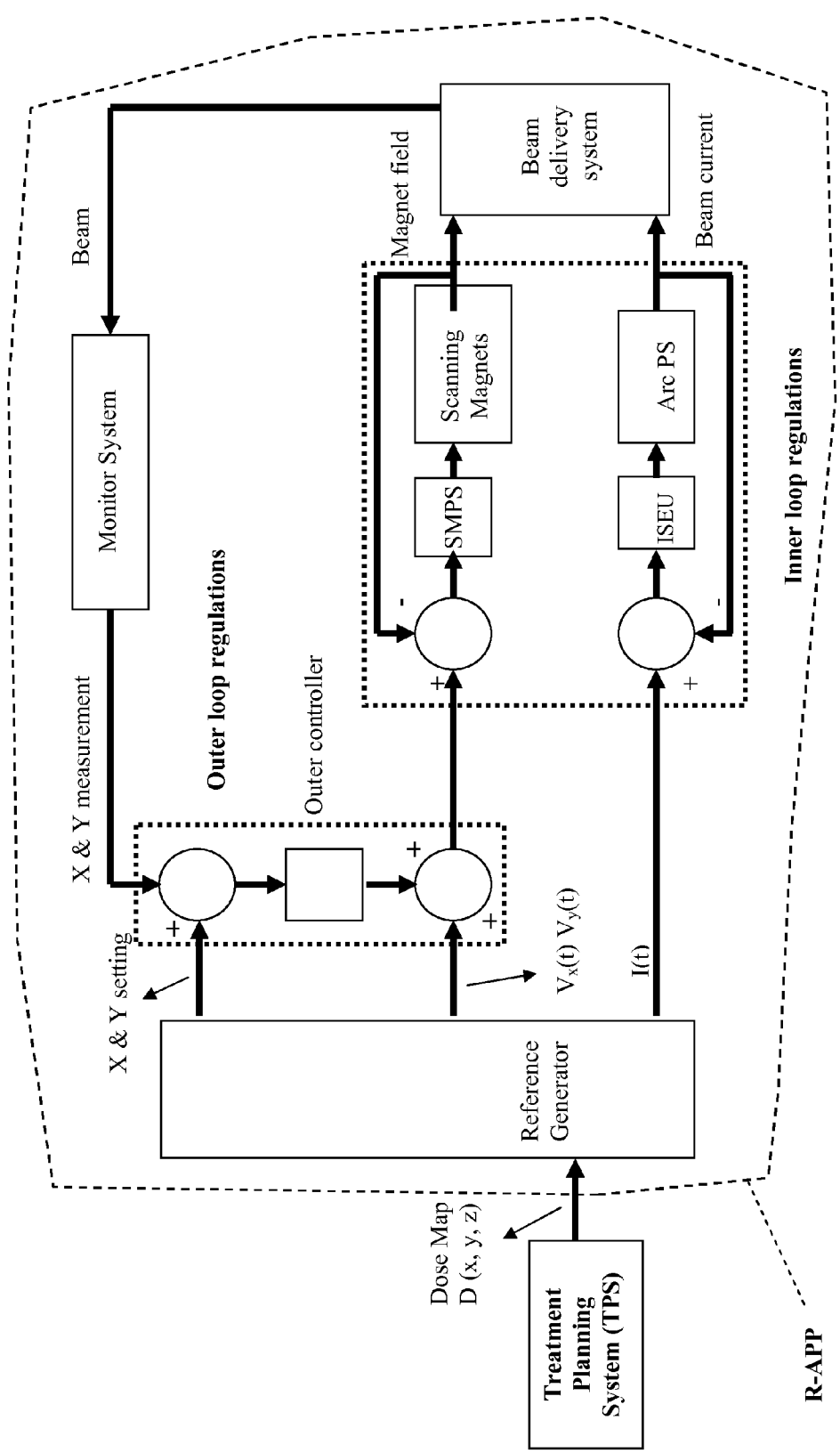
FIG. 1A shows a schematic view of a radiation apparatus as disclosed in WO 03/101538A1.
Figure 1:
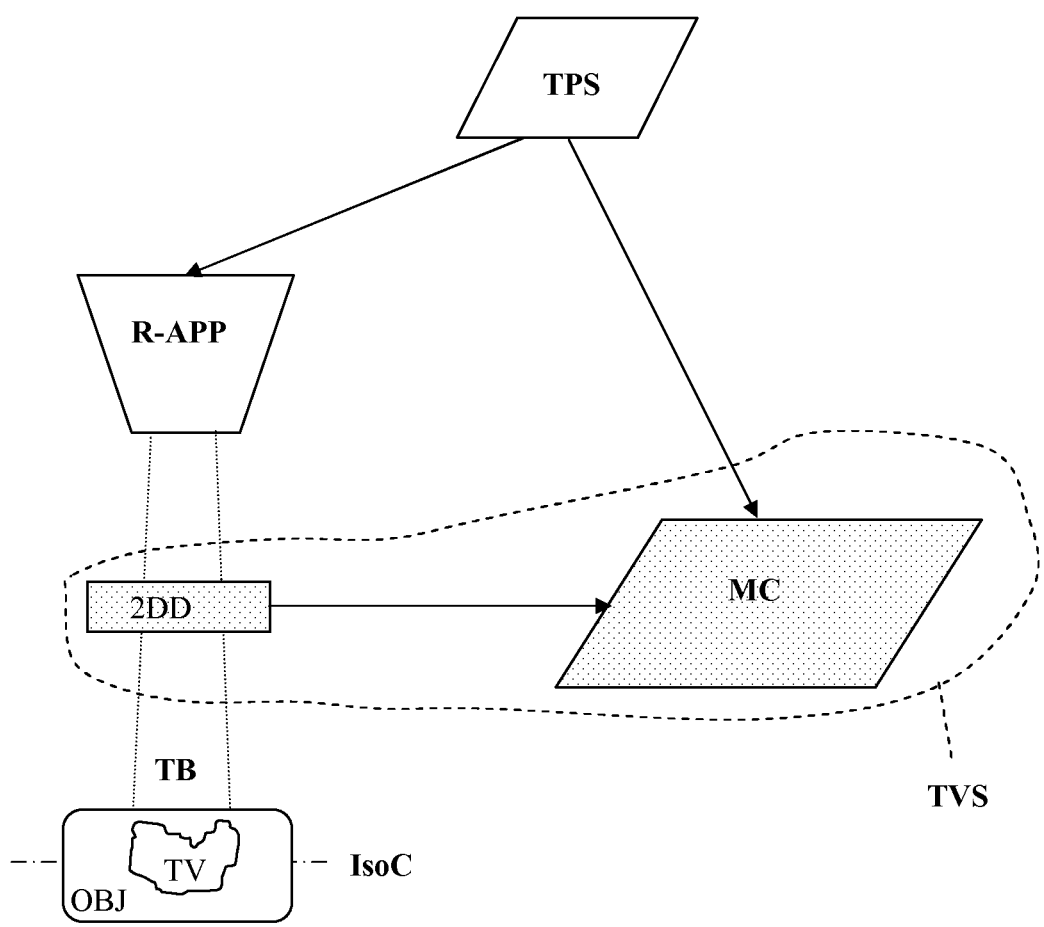
FIG. 1B shows a schematic view of a device, named TVS (Treatment Verification System), according to the invention, in relation to its environment.

According to the preferred embodiment, shown schematically in FIG. 1B, the present invention is intended to be used with a particle radiation apparatus (R-APP), which delivers treatment beams (TB) to a target volume (TV) positioned at the isocentric plane (IsoC). The target volume can be part of an object (OBJ) where the object is e.g. a phantom or a patient. The treatment beams are characterized by a set of treatment beam parameters defined by a treatment planning system (TPS). Using a gantry system or a set of fixed beam lines, multiple treatment beams can be delivered from different entry angles during the same treatment fraction. The present invention, hereafter named Treatment Verification System (TVS) and as enclosed on FIG. 1B with a dotted line, comprises a 2D detector (2DD) and a main controller (MC). The 2D detector is positioned orthogonally with respect to the central axis of the treatment beam and is installed inbetween the RT-APP and the target volume. The 2D detector can either be fixed to the RT-APP and rotate together with the gantry or it can be kept in place by an external holder (not rotating with the gantry). When no target is present, the detector may also be positioned at the IsoC. The main controller comprises a user interface, a data acquisition system to measure the 2D detector responses in real time, a TVS commissioning module to configure the TVS for a specific particle radiation apparatus, a treatment plan import module to import a treatment plan from an external system (in a convenient format, such as DICOM format), a 2D detector response predicting module, a 2D detector response comparison module, an error handling module, a 3D dose calculating module and a dose tracking module.

The TVS operates independently from the R-APP controls except for optionally receiving synchronisation signals from the R-APP for synchronising the data acquisition of the 2D detector device with the treatment beam delivery. Hence, the proposed invention consists of a treatment verification system that may be added to any existing particle radiation apparatus.

In an alternative embodiment of the present invention, the TVS can further be equipped with a dedicated additional detector to measure the particle energy or the water-equivalent range of the particles. Different options to install this additional energy detector are possible. The energy detector can be installed downstream with respect to the 2D detector (e.g. on the back of the 2D detector) where it can either stay permanently in the beam path or be brought in/out of the beam path using a movable arm. The energy detector can alternatively be installed aside of the 2D detector. The energy detector can be a multi-layer Faraday cup as described by Gottschalk and R. Platais in "Nuclear interactions of 160 MeV protons stopping in copper: A test of Monte Carlo nuclear Models", Med. Phys. 26, 2597-2601 (1999). Alternatively, the energy detector can also be constructed based on a stack of ionisation chambers.

Figure 2:
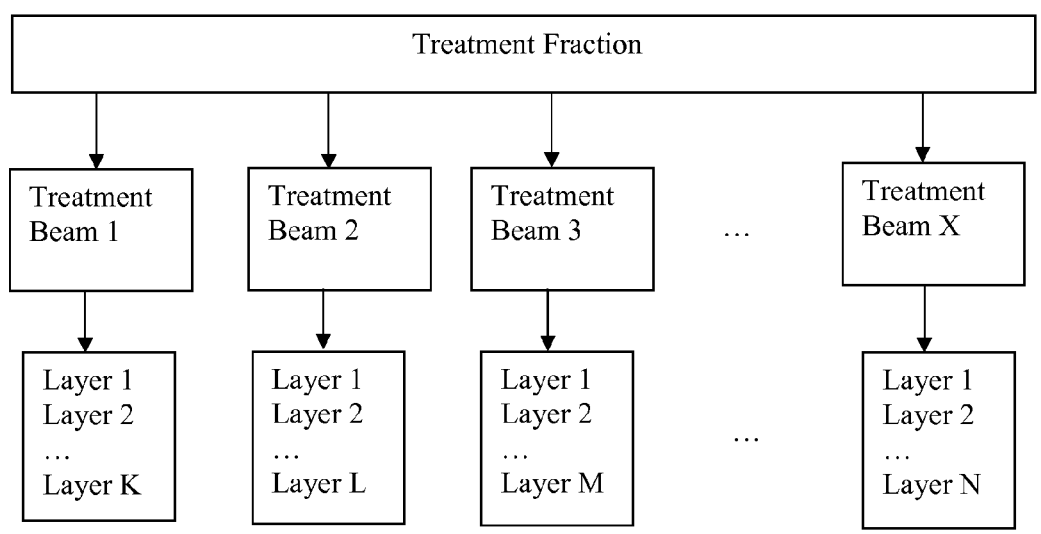
FIG. 2 is a representation of data structure.

The set of treatment beam parameters defined by a TPS depends on the specific beam delivery technique applied by the particle therapy apparatus. The preferred embodiment of the invention is the use of a particle radiation treatment apparatus applying intensity modulation as described by Lomax et al, "Intensity modulation methods for proton radiotherapy", Phys. Med. Biol. 44 (1999) 185-205. When applying such a technique the intensity variation is a three dimensional problem: the pencil beam intensity or beam spot intensity can vary across a plane perpendicular to the central beam axis and the intensity can also be varied as a function of the particle energy, specifying the penetration depth of the particle in the target volume. Hence, the treatment beam parameters defined by the TPS need to comprise a three dimensional intensity matrix specifying in each voxel the integral particle fluence to be delivered for the given beam. Such a 3D matrix is translated in a sequence of locations, extensions, intensities or weights of each individual pencil beam with a given energy to be delivered by the particle radiation apparatus for the given beam. For practical purposes and as specified by the DICOM standard, each treatment beam can be further sub-divided in a set of layers, each layer being specified by the prescribed particle energy, as illustrated in FIG. 2. Each layer is then specified by a two-dimensional intensity or fluence matrix: for each beam position in the given layer (X,Y), the number of required particles or fluence is prescribed. This particle weight matrix prescribes the number of particles in air or in another material at a reference plane perpendicular to the central beam axis (e.g. at IsoC) to be delivered by the particle radiation treatment apparatus for the specified particle energy. The treatment beam layer parameters comprise besides the two-dimensional layer intensity matrix also a series of parameters related to the characteristics of the particle beam (e.g. the particle beam spot size or particle spot distribution specified at a reference position, the particle energy).

When a treatment beam is sub-divided in treatment sub beams defining a layer irradiation as discussed above and illustrated in FIG. 2, it does not mean that all particles of a specific layer forming a particle sub beam are mono-energetic. Each sub beam defining a layer irradiation has a certain energy spread. The energy spread of the beam can be influenced by several components of the radiation apparatus (e.g. accelerator, energy adjusting devices, any material in the beam line and beam delivery system such as monitor detectors, . . . ).

In general, rather than characterising a particle beam by its energy one characterises a particle beam by its water-equivalent penetration depth or range expressed in $g/cm^2$. The nominal range of a particle beam or Bragg peak is then defined as the range where the Bragg peak intensity drops below a given value (for example the 90% or 80% range value). When a layer is characterized by an energy, this has to be interpreted as the energy corresponding to the 80% or 90% maximum penetration depth (other definitions for defining the range can be used as well).

Remark that when a pencil beam technique is applied, one often uses so-called ridge filters to reduce the number of layers to be applied to cover a given depth of the target volume. Indeed, especially at lower beam energies the Bragg peaks become very thin and as a result the number of layers or number or Bragg peaks needed to cover a given depth of the target volume can become very large. The effect of using a ridge filter is that the peak width of the Bragg peak is smeared out or extended and in this way the number of layers can be reduced. The current device and method of invention also applies when ridge filters are used. The ridge filters are taken into account by the treatment planning system. Of course the spread in energy of the particles has become larger than when no-ridge filter is used. In general, as mentioned above, rather than characterising a sub beam by an energy one characterises a sub beam, corresponding to a layer irradiation, by its water-equivalent penetration depth or range. The characterizing range of the sub beam is then defined as the range where the Bragg peak intensity drops below a given value (e.g. 90% or 80% range value). This definition for characterizing a layer can still be used when a ridge filter is used and hence the concept of specifying treatment beam layer parameters on the level of the treatment planning as illustrated in FIG. 2 is still valid in the context of using ridge filters. Another parameter that can be introduced on the layer level is the amount the Bragg peak is spread out or the thickness of the layers which can also be expressed as a water equivalent thickness in $g/cm^2$.

In a preferred embodiment of the invention, a 2-dimensional ("2D") radiation-transparent electronic detector is required to provide a 2-dimensional map of measurements on a plane orthogonal to the treatment beam direction, but without causing a relevant perturbation of the therapeutic treatment beam. A technology used to realize such a detector for hadron beams is described by Bonin and al. in "A pixel chamber to monitor the beam performances in hadron therapy", Nuclear Instruments and Methods in Physics research, A 519 (2004)-674-686. This document describes a device made up of a 2-D array of 1024 ionisation chambers arranged in a regular matrix of 32×32 pixels. This technology is also used in the commercial product MatriXX manufactured by the Applicant. Although the preferred embodiment is the use of an ionization pixel chamber, the present invention can also be realised with other type of 2D electronic detectors such as for example the use of a scintillator detector and CCD camera. Such a technology is described by Frelin et al. in "The DosiMap, a new 2D scintillating dosimeter for IMRT quality assurance: Characterization of tow Cerenkov discrimination methods", Med. Phys. Vol. 35, No. 5, (1998), 1651-1662. A detection technique using a gaseous scintillation detector is described by Timmer et al in "A scintillating GEM for 2D-dosimetry in radiation therapy", Nucl. Instr. and Methods in Physics Research Section A, Volume 478, (2002), 98-103. These scintillator based detectors may not be radiation transparent.

Figure 3:
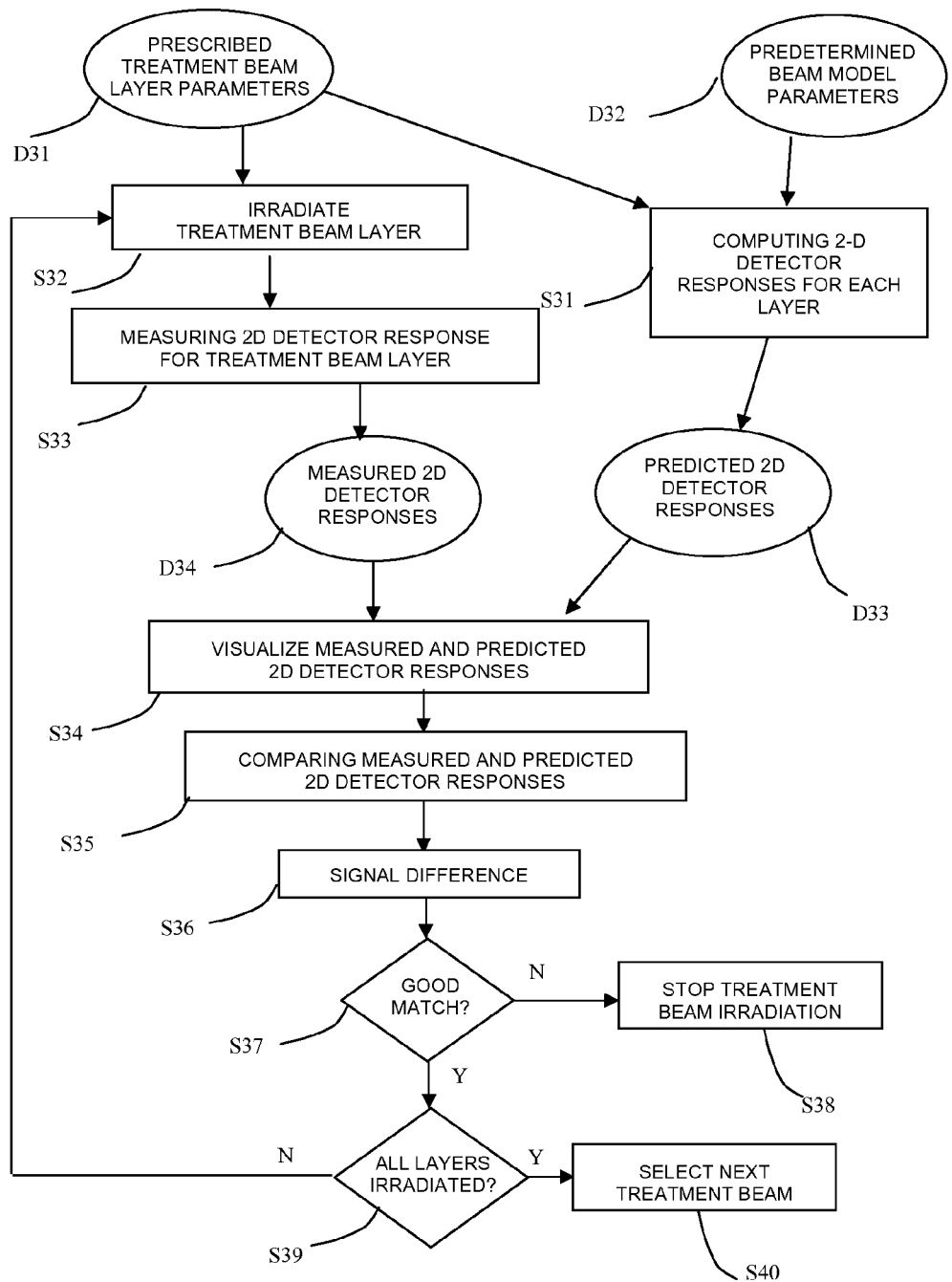
FIG. 3 is a dataflow diagram which represents a method for comparing predicted and measured 2D detector responses.

The method according to the present invention is schematically shown in FIG. 3. A treatment plan for irradiating a target volume is made with a TPS. The outcome of a treatment planning calculation is information that will be used by the particle radiation apparatus and it specifies the characteristics of the treatment beams to be delivered within a treatment fraction through a set of prescribed treatment beam layer parameters (D31). Following step S31, the 2D detector response predicting module of the TVS computes the 2D detector responses for each layer of the treatment beams. In a first step the particle fluence calculation device computes the particle fluence at the 2D detector position using the set of prescribed treatment beam parameters (D31) as input data and by using a beam model with a set of predetermined beam model parameters (D32). In a second step the 2D detector response calculation device computes the 2D detector responses (D33) using the particle fluence at the 2D detector position as input data and by using a detector model describing the geometry of the 2D detector and a detector response model describing the response of the 2D detector to particle irradiation. The particle radiation apparatus delivers the treatment beam on a layer per layer basis (S32). During the irradiation, the 2D detector measures the 2D detector responses (S33) and the TVS acquires and stores the measured responses in a memory (D34). The measured and predicted 2D detector responses can be visualized (S34). After completion of a layer irradiation, the measured and predicted 2D detector responses are compared (S35) and differences in 2D responses are signalled (S36). Based on the information signalled by the TVS (S36), the operator can decide to stop the treatment beam irradiation if the differences between the measured and predicted 2D responses are out of tolerances (S38). If the comparison is within tolerance (test S37 positive), the next layer of the irradiation is performed (test S39 negative). This sequence is repeated until all treatment beams have been processed (S40).

Figure 4:
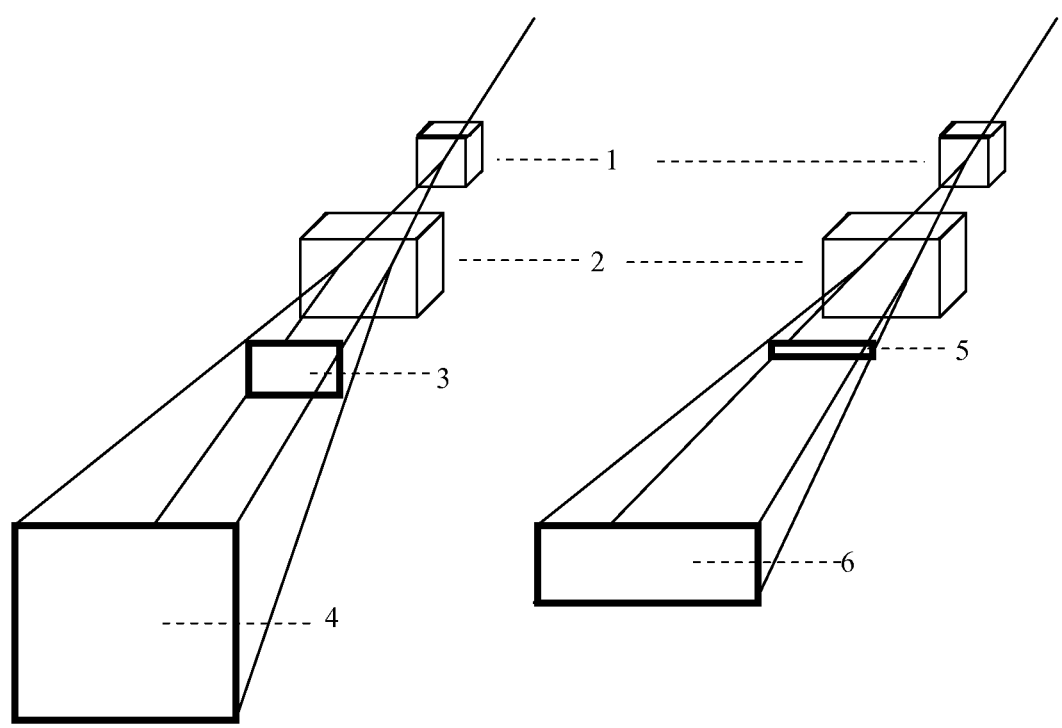
FIG. 4 shows schematically a distortion in the shape of the treatment beam resulting from an error in one of the scanning magnets.
Figure 5:
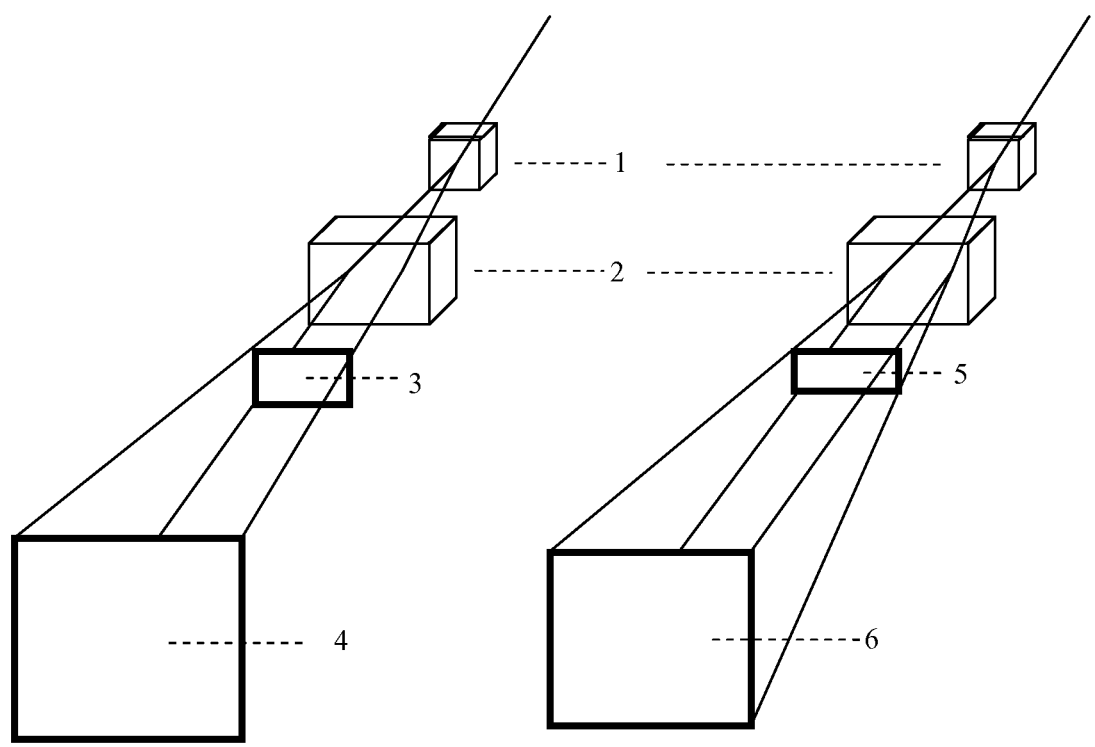
FIG. 5 shows schematically a distortion in the shape of the treatment beam resulting from an error in the particle energy.

According to the preferred embodiment of the present invention the TVS can identify errors of the particle radiation apparatus when discrepancies larger than the accepted clinical tolerances between the measured 2D detector responses and the predicted 2D detector responses occur. An example of a discrepancy that can occur is a distortion in the shape of the treatment beam layer. Distortions can occur for example due to the malfunction of the beam scanning magnets as illustrated in FIG. 4. In FIG. 4, two scanning magnets in two orthogonal directions are represented (1 and 2), a rectangular treatment beam is delivered at isocenter (4) and the response of the treatment beam at the position of the 2D detector is shown in 3. On the right side of the figure a distorted treatment beam is shown. When there is for example a failure in the vertical scanning magnet, the distortion of the treatment beam 6 is observed at the position of the 2D detector 5. Another example of distortions are the ones due to errors in the particle energy as illustrated in FIG. 5. A change in particle energy implies a change in the particle magnetic rigidity. These results in a distortion of the shape of the 2D treatment beam layer and consequently in distortions of the 2D measured detector responses (5). In case of such an energy error, there is a correlation of the distortions in the two scanning directions, depending on the geometry and position in respect to isocenter of the two scanning magnets. The TVS comprises an energy calculating device in its error handling module to examine distortions in the shape of the measured 2D detector responses when compared with the said predicted 2D detector responses. Based on the observed distortions, the TVS can deduce the variation in energy of the particles with respect to the prescribed particle energy.

The TVS uses standard beam modelling techniques comprising a particle fluence calculation device and a dose calculation device. The details of the beam model vary in general with the type of beam delivery technique applied (e.g. a passive scattering technique or a scanning technique). The preferred embodiment of the invention is for use with a particle scanning technique. As is the case for a standard TPS, to adapt the generic beam model to a given therapy apparatus, a set of measurements of the delivery characteristics of the given therapy apparatus need to be performed during a so-called TVS commissioning phase. These measurements allow to establish a set of parameters of the beam model that represent a valid set for the given apparatus for any possible configuration. The beam model parameters are optimised in order to give the best match between model predictions and measured data. Examples of data to be measured are: depth dose curves, the phase space of the particle pencil beam, the particle energy spectrum, . . . . The result of this TVS commissioning phase is a set of predefined beam model parameters. Useful descriptions of beam modelling techniques for scanned particle beams are provided, for example, by Kimstrand et al, "A beam source model for scanned proton beams", Phys. Med. Biol. 52 (2007), 3151-3168, or by E. Pedroni et al, "Experimental characterization and physical modelling of the dose distribution of scanned proton pencil beams", Phys. Med. Biol. 50 (2005) 541-561. In addition, during the TVS commissioning, the accuracy of the 2D detector response predicting module can be verified experimentally using a set of standard treatment beams (e.g. geometrical shapes) and by comparing the predicted 2D responses with the measured 2D responses. Measurements can be performed with the 2D detector positioned at different distances from isocenter. An iterative approach can be followed to update the beam model and/or detector model to optimize the matching of the 2D responses.

According to the preferred embodiment of the invention, the TVS predicts 2D detector responses using a 2D detector response predicting module. The input data for this calculation are the prescribed treatment beam parameters defined by the treatment planning system. The 2D detector response predicting module uses a beam model, a set of predetermined beam model parameters, a 2D detector model and a detector response calculating algorithm to specify the 2D detector responses. As part of the beam model, the distance between the 2D detector and the isocenter is defined. The TVS beam model comprises a 2D detector particle fluence calculation device which calculates the particle fluence at the 2D detector position. The particle fluence can be calculated by a combination of the phase space of a single beam spot at the detector position and a two-dimensional beam spot weight map defined at the detector position. The phase space of a single beam spot characterizes the divergence and beam size of the pencil beam at the detector position. This phase space can be measured during commissioning for a series of 2D detector positions, be modelled and be part of the beam model. The two-dimensional weight map at detector position can, by geometrical reconstruction by the beam model, be calculated based on the two-dimensional weight map defined at isocenter which is part of the treatment beam parameters, defined by the TPS. The calculated particle fluence derived from the two-dimensional weight map and from the relative phase spaces of all the beam spots at the 2D detector plane is then used to define the predicted 2D detector responses using a detector model describing the geometry of the device and a response calculation algorithm describing the device response to particle irradiation. Alternatively other model approaches and algorithms can be followed to calculate the 2D detector responses. The fluence calculation and/or 2D detector response calculation can also be computed following a Monte Carlo method.

The preferred embodiment of the invention uses an algorithm to compare the measured and predicted 2D detector responses. Different algorithms can be used to perform a comparison. A more qualitative approach is to visualize a two-dimensional response-difference map obtained by subtracting the predicted 2D detector response from the measured 2D detector response. More quantitative comparisons will be made as well. A first verification is performed by making the integral of the measured responses of all pixels and comparing with the predicted integral. A second verification is a relative verification of the 2D response distribution to evaluate the overall quality of the matching between the measured and predicted 2D responses. For this purpose, the principle of the gamma-index formalism, which is generally used to compare two-dimensional dose distributions, can be applied. The gamma-index formalism is described by Low et al, Med. Phys. 25 (5), May 1998.

Figure 6:
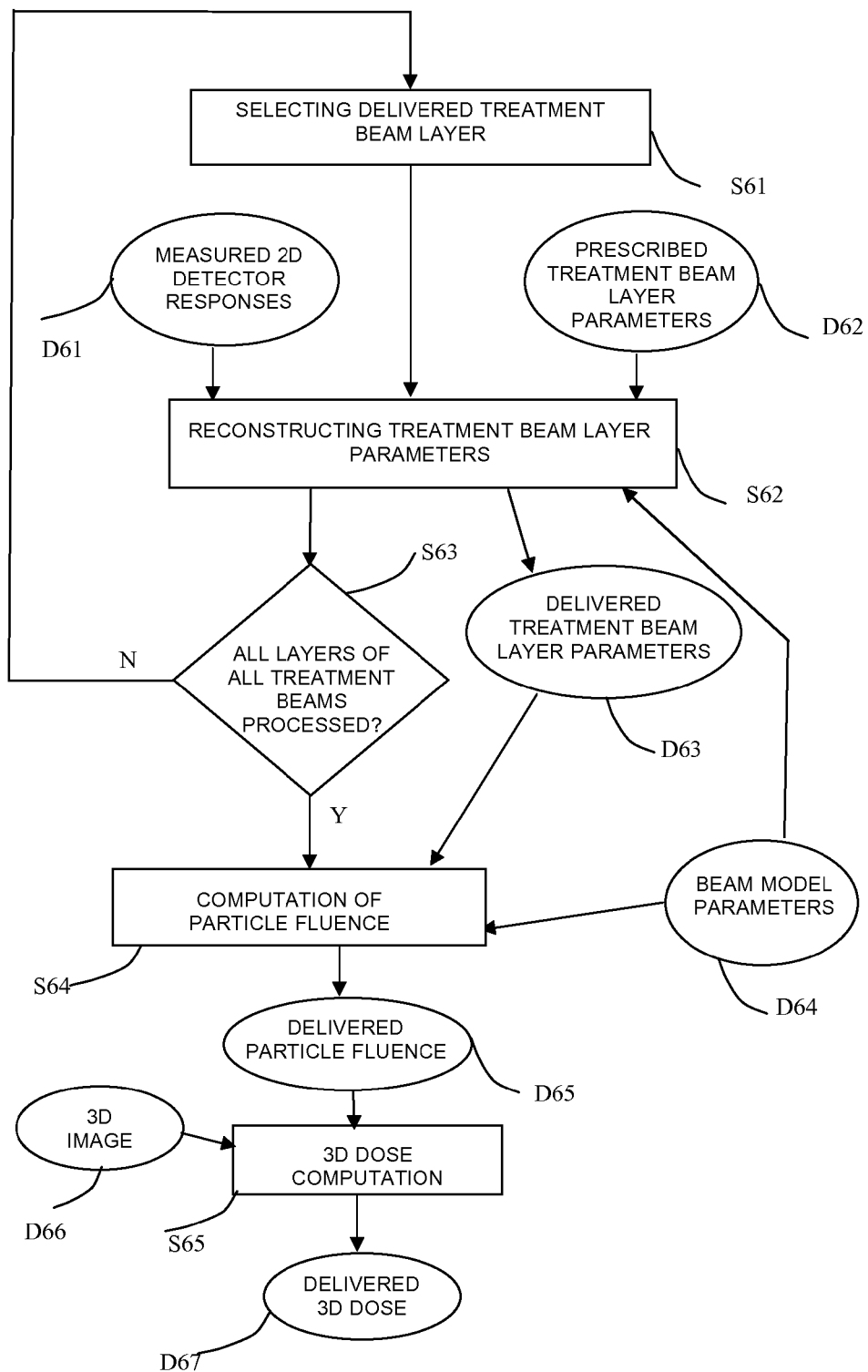
FIG. 6 is a dataflow diagram which represents a method for determining the delivered 3D dose distribution in an object based on measured 2D detector responses.

According to the preferred embodiment of the present invention, the 3D dose distribution in the target volume based on the measured 2D detector responses can be reconstructed. FIG. 6 is an example of a dataflow diagram representing this method. For each layer of the treatment beam (S61) the delivered treatment beam layer parameters (D63) are reconstructed (S62) by the beam model using the beam model parameters (D64). The delivered treatment beam parameters are defined at a reference position or reference plane. The measured 2D detector responses (D61) are basically a convolution of the particle intensity map at the detector position with the particle spot distribution (for example a 2D Gaussian shape with a spot sigma defined in the prescribed treatment beam layer parameters). One method is to perform a deconvolution of the 2D detector responses taking into account the beam size of the beam at the detector position. For a given prescribed beam size at the isocenter, defined by the prescribed treatment beam layer parameters (D62), the beam size can be calculated at the 2D detector position using the beam model and detector geometry. After the deconvolution of the 2D detector responses, a delivered 2D intensity map at isocenter can be reconstructed. The delivered energy of the particles for each layer are obtained from the energy detector. In this way a new set of treatment beam layer parameters are reconstructed by the beam model, called delivered treatment beam layer parameters (D63), comprising the delivered 2D intensity map and the delivered particle energy. This sequence of specifying delivered treatment beam layer parameters is repeated until all layers of all treatment beams are processed (S63). These delivered treatment beam layer parameters (D63) are then used as an input together with a beam model and associated beam model parameters (D64) to calculate the particle fluence through the object (S64), further named delivered particle fluence (D65). The delivered particle fluence (D65) together with the 3D image (D66), representing a description of the target volume geometry and density and organs at risk, is used to calculate (S65) the delivered 3D dose distribution (D67) in the target with the TVS dose calculation device applying a dose model.

In another embodiment, the particle fluence computation and/or 3D dose computation can be performed with a Monte Carlo method.

Figure 7:
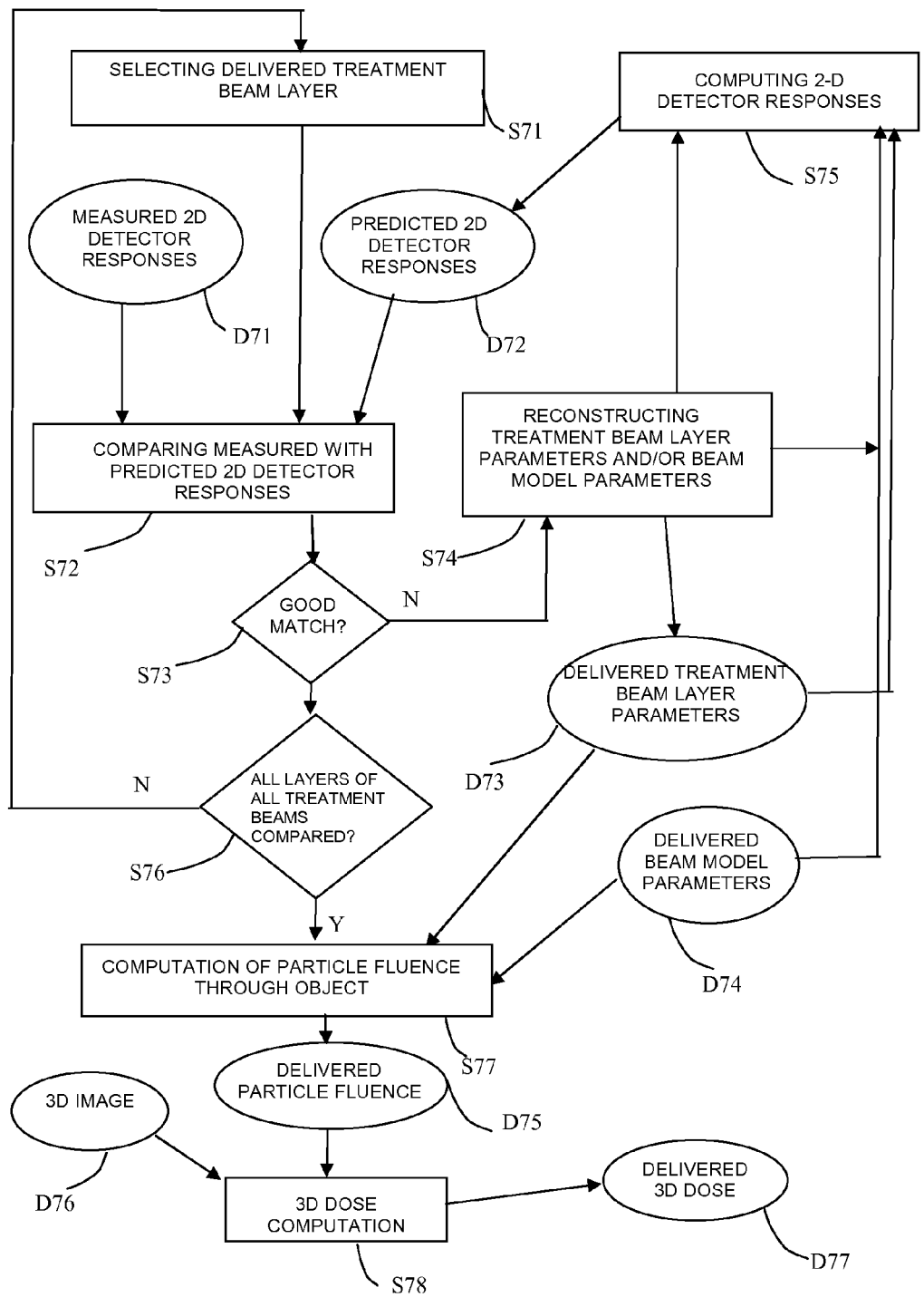
FIG. 7 is a dataflow diagram which represents another method for determining the delivered 3D dose distribution in an object based on measured 2D detector responses.

Alternatively, another method to obtain the 3D delivered dose distribution is presented in FIG. 7. This is an iterative approach where treatment beam layer parameters (selected in step S71) and/or beam model parameters are adjusted until a good match between the measured and predicted 2D detector responses is obtained. The measured 2D detector responses (D71) are compared with predicted 2D detector responses (D72) by a scoring function quantifying the difference between them (S72). The predicted 2D detector responses are initially calculated based on the prescribed treatment beam parameters from the TPS and the predefined beam model parameters obtained from the TVS commissioning. When the 2D comparison is not within a predefined scoring limit (test S73 negative), an iterative process starts and treatment beam parameters and/or beam model parameters are adjusted (S74) and are named delivered treatment beam parameters (D73) and/or delivered beam model parameters (D74), respectively. With these new sets of parameters (D73, D74) the 2D detector responses are calculated (S75), and a new comparison with the measured 2D detector responses is performed (S72). Should this iterative modification of the treatment beam parameters and/or beam model parameters converge to a sufficiently small difference in the scoring function, it is considered that the last modified treatment beam parameters and/or beam model parameters faithfully represent the delivered treatment beam. As this iterative process is performed for each treatment beam layer, until test S76 is positive, delivered beam model parameters (D74) are specified for each layer. These delivered treatment beam layer parameters (D73) and/or delivered beam model parameters are then used as an input to calculate the particle fluence through the object (S77, D75). The delivered particle fluence (D75) together with the 3D image (D76), representing a description of the target volume geometry and density and organs at risk, is used to calculate the 3D dose distribution (D77) in the target with the TVS dose calculation device (S78) applying a dose model.

The iterative method described in FIG. 7 could also not converge, in which case there are no reconstructed or delivered treatment beam parameters and/or delivered beam model parameters, but rather an indication of failure. This would typically occur if the measured response is very different from the predicted one, i.e. if the wrong plan is delivered, if significant failures of the particle radiation apparatus occur (e.g. wrong calibration of scanning magnets, wrong particle beam energy, . . . ).

The beam parameters and/or beam model parameters that can be modified during the iterative optimization method (S74) and the maximum allowable deviations from the nominal values could be specified. Typical examples of treatment beam layer parameters that can be modified are the positions X,Y, beam weights in the layer weight map and the beam size. Examples of beam model parameters that could be modified are the beam centralization, a parameter specifying how well the particle beam is centered with respect to the central beam line, the energy spread of the particles, beam source position and size, etc. . . .

When a dedicated detector is used to measure for each layer the energy of the particles, the measured energy of each layer can be used as an input for calculating delivered particle layer fluences and/or the delivered 3D dose distribution. If no dedicated energy detector is used to measure directly the energy of the particles, the particle energy is also a treatment beam layer parameter that can be optimized with the iterative process presented in FIG. 7 and the particle energy is computed with the energy calculating device based on distortions in the shape of the 2D detector responses.

According to the preferred embodiment of the invention, the TVS can import the planned 3D dose distribution in the object as calculated by an external treatment planning system. This initially planned 3D dose distribution can be compared with the delivered 3D dose distribution as computed by the TVS. When the target is an homogeneous water phantom, the comparison between the 3D delivered dose distributions with the predicted 3D dose distributions permits on the one hand to extract a report of parameters for assessing the quality of the delivery of the RT apparatus (flatness, symmetry, penumbra, field shaping, leaves position, . . . ), and on the other hand to identify possible causes of errors due to mismatches in said comparison or errors due to unexpected parameter values in said report of parameters.

A 3D dose distribution constitutes a large data set, typically in the order of a million or more data points. Comparing two such distributions therefore requires dedicated tools. One possible set of such tools comprises different types of dose volume statistics, typically based on predefined volumes (regions) of interest. The most common dose volume tool is the dose volume histogram (DVH) analysis. Another set of tools are based on extracting 2D subsets from the 3D data. The 2D subsets typically constitute planes normal to the major axes (parallel or orthogonal to the beam direction). On such planes, the 2D dose distribution can be represented by color codes, isodose lines or as a 3D surface. Lines can be defined on the planes and the dose can be extracted along these lines as 1D subsets, and displayed in graphs. Furthermore, point-by-point information such as the dose value in a given point and its coordinates can be obtained by selecting a point either on a plane or on a line. The 2D subset corresponding to the same planes of the measured and of the planned 3D data can be compared one another using the gamma analysis or performing other operations like point by point ratio, differences, etc. Similar operations can be performed on the 1D subsets.

The TVS also allows to perform 3D dose tracking as a function of the delivered fractions. The 3D dose distributions delivered during each treatment fraction are stored in a memory. The delivered 3D dose distributions during subsequent treatment fractions can then be accumulated and visualized in the object.

In addition, the TVS can acquire an updated description or image of the object coming from newly taken CT scan data or from other imaging devices (e.g. Cone Beam CT). The TVS can then visualize the delivered 3D dose distribution with the updated object images and produce analysis like dose volume histograms cumulated over the delivered fractions taking into account eventual deformations of the clinical targets.

Accordingly, many advantages are reached by using the present invention. In fact the embodiments of the invention allow to:
  quickly detecting possible delivery and/or planning errors during QA and patient plan verification;
  perform a 3D dose verification of the delivered irradiation in the patient's anatomy which is independent of original TPS, by using patient's anatomy data, a dose algorithm independent from the TPS and the input of the measured detector responses;
  provide the oncologist with data analysis tools in order to perform studies of protocols for given tumour entities and to compare results from different TPSs and radiation sources;
  verify the delivered dose distribution directly on the patient anatomy and not only in homogeneous phantoms.
  reduce global costs due to the cumbersome and long lasting state-of-art measurements and routine equipment QA tests;
  either use the device in a method to verify treatment beam delivery prior to patient irradiation or to use the device in the method of the invention to verify treatment beam delivery during patient irradiation.

The invention claimed is:
1. A device for monitoring and verification of treatment beam delivery to a target, with a particle radiation apparatus, said treatment beam comprising one or more treatment sub beams corresponding one or more treatment beam layers, said treatment beam layers being characterized by a set of treatment beam layer parameters, said particle radiation apparatus being configurable for a given set of treatment beam layer parameters, said device comprising:
  an acquirer configured to acquire treatment beam layer parameters for said one or more treatment beam layers;
  an electronic 2D detector device configured to:
    be placed between the particle irradiation apparatus and the target, and
    measure 2D responses of said treatment beam layer in a plane essentially perpendicular to the central axis of said treatment beam;

a 2D detector response predicting module configured to determine predicted 2D detector responses for said one or more treatment beam layers to be delivered with said particle radiation apparatus configured with said given set of treatment beam layer parameters;

a memory to store the predicted 2D detector responses of each said one or more treatment beam layers;

an acquirer configured to acquire in real time the 2D detector responses caused by said one or more treatment beam layers delivered by said particle radiation apparatus being configured with said given set of treatment beam layer parameters;

a 2D detector response comparison module configured to perform a comparison between the measured 2D detector responses and the corresponding said predicted 2D detector responses; and an error handling module configured to signal the difference between said measured 2D detector responses and said predicted 2D detector responses, and wherein said 2D detector response predicting module further comprises:

a 2D detector fluence calculation device configured to calculate the particle fluence at the 2D detector position for said treatment beam layer parameters; said article fluence calculation device comprising a beam model said beam model being based on a set of beam model parameters, said beam model parameters comprising characteristics of the particle radiation apparatus and said particles;

a 2D detector response calculation device configured to calculate for a given said article fluence at the 2D detector position the corresponding 2D detector responses said 2D detector response calculation device comprising a detector model of said 2D detector device describing the geometry of the 2D detector and a detector response model describing the response of the 2D detector to particle irradiation.

2. The device according to claim 1 wherein said 2D detector fluence calculation device and/or said 2D detector response calculation device is based on a Monte Carlo algorithm calculating the particle fluence at the 2D detector position or calculating the 2D detector responses.

3. The device according to claim 1 further comprising a measurer configured to measure the energy of particles of a said treatment beam layer.

4. The device according to claim 3, wherein the measurer comprises a particle range detector, said particle range detector configured to measure the particle waterequivalent range, said particle waterequivalent range being a function of said particle energy.

5. The device according to claim 3, wherein the measurer further comprises an energy calculating device, said energy calculating device being based on examining distortions in the shape of the measured 2D detector responses when compared with the predicted 2D detector responses, said distortions being function of variations in said energy.

6. The device according to claim 1, wherein the device further comprises:

an importer configured to import a description of the target volume in an object, said description comprising the 3D shape, density distribution and position of the target volume and/or organs at risk within the object;

a treatment beam parameter reconstructing device configured to compute for the one or more delivered treatment beam layers the delivered treatment beam layer parameters based on the measured 2D detector responses of the one or more layers and a beam model, said beam model being characterized by a set of beam model parameters;

a particle fluence calculation device configured to calculate for the one or more delivered treatment beam layers the delivered layer particle fluence through the object based on the delivered treatment beam layer parameters and said beam model;

a dose calculation device configured to compute the delivered 3D dose distribution within the object, said 3D dose distribution resulting from one or more delivered treatment beams, said delivered treatment beam comprising one or more said delivered treatment beam layers, said computing the delivered 3D dose distribution being based on said delivered layer particle fluence of the one or more layers of said treatment beam; and a display configured to display the delivered 3D dose distribution in the object.

7. The device according to claim 6, wherein:

said treatment beam parameter reconstructing device further comprises an iterative algorithm configured to update the beam model parameters and/or said layer treatment beam parameters until the comparison between the measured 2D detector responses and the corresponding predicted 2D detector responses minimizes a scoring function and assign the new values of beam model and/or treatment beam layer parameters, obtained after minimizing the scoring function, as the delivered beam model parameters and/or delivered treatment beam layer parameters; and said particle fluence calculation device configured to calculate for the one or more delivered treatment beam layers the delivered layer particle fluence through the object is using the delivered treatment beam layer parameters and the delivered beam model parameters.

8. The device according to claim 6 further comprising:

an importer configured to import the planned 3D dose distribution in the object as calculated by an external treatment planning system;

a comparer configured to compare the planned 3D dose distribution with the delivered 3D dose distribution; and a reporter configured to report a set of parameters resulting from said comparison.

9. The device according to claim 6 further comprising:

a memory configured to store the delivered 3D dose distribution delivered during a treatment fraction;

an accumulator configured to accumulate the delivered 3D dose distributions delivered during subsequent treatment fractions; and a display configured to display the accumulated 3D dose distribution in the object.

10. The device according to claim 9 further comprising:

an acquirer configured to acquire an updated description or image of an object;

a memory configured to store the updated description or image of the object; and a display configured to display the accumulated 3D dose distribution with the updated description or image of the object.

11. The device according to claim 1, further comprising an input module for importing a treatment plan from an external device, said treatment plan comprising a plurality of plan parameters, said plurality of plan parameters comprising said treatment beam layer parameters, said a description of the target volume in an object, said planned 3D dose distribution.

12. The device according to claim 1, wherein the device is configured to operate independently from the particle radiation apparatus, receiving only a treatment plan from an external device.

13. The device according to claim 1, further comprising a commissioning module to optimize said set of beam model parameters based on measured data with the particle radiation apparatus.

14. A method for verifying treatment beam delivery from a particle radiation apparatus prior to the irradiation of a target, said method comprising:

providing a particle radiation apparatus for delivery of a treatment beam to the target, said treatment beam comprising one or more treatment sub beams, the one or more treatment sub beams being defined as a treatment beam layer corresponding to an irradiation layer and comprising particles having essentially the same energy, the one or more treatment beam layers being characterized by a set of treatment beam layer parameters, said particle radiation apparatus being configurable for a given set of treatment beam layer parameters, providing an acquirer configured to acquire prescribed treatment beam layer parameters;

providing, between the particle irradiation apparatus and the target, a 2D detector device configured to provide a measured 2D detector response of said treatment beam layer in a plane perpendicular to the central axis of said treatment beam;

for the one or more beam layers, determining a predicted 2D detector response for said prescribed treatment beam layer parameters, said step of determining a predicted 2D detector response compromising:

computing the particle fluence at the 2D detector position using the set of prescribed treatment beam layer parameters as input data and by using a beam model with a set of predetermined beam model parameters, computing the predicted 2D detector response using the particle fluence at the 2D detector position as input data and by using a detector model describing the geometry of the 2D detector and a detector response model describing the response of the 2D detector to particle irradiation;

delivering said treatment beam layer to the target with said particle radiation apparatus being configured with said prescribed treatment beam layer parameters;

measuring the 2D detector responses caused by the treatment beam layer delivered by said particle radiation apparatus;

performing a comparison between the measured 2D detector response and the corresponding predicted 2D detector response; and signalling difference between said measured 2D detector response and said predicted 2D detector response.

15. The method according to claim 14, wherein the method further comprises:

providing a measurer configured to determine the layer energy of a treatment beam layer;

for the one or more beam layers:

determining the delivered layer energy of the particles;

performing a comparison between the delivered layer energy and the prescribed layer energy, the prescribed layer energy being part of the treatment beam layer parameters; and signalling difference between said measured layer energy and said prescribed layer energy.

16. The method according to claim 14, wherein the method further comprises:

providing a description of a target volume in an object, said description comprising the 3D shape, density distribution and position of the target volume within the object;

computing for the one or more delivered treatment beam layer layers the corresponding delivered treatment beam layer parameters based on the measured 2D detector responses of the one or more beam layers and a beam model, said beam model being characterized by a set of beam model parameters;

computing for the one or more delivered treatment beam layers the delivered layer particle fluence through the object based on the delivered treatment beam layer parameters and the beam model;

computing the delivered 3D dose distribution within the object, said 3D dose distribution resulting from one or more delivered treatment beams, the delivered treatment beam comprising one or more delivered treatment beam layers, said computing the delivered 3D dose distribution is based on said delivered layer particle fluence of the one or more layers of the treatment beam; and displaying the delivered 3D dose distribution in the object.

17. A method according to claim 16, wherein the step of computing delivered treatment beam parameters comprises:

a. providing new values for said treatment beam layer parameters and/or said beam model parameters;

b. obtaining new predicted 2D detector responses based on new values for said treatment beam layer parameters and/or beam model parameters;

c. repeating steps a and b until the comparison between the measured 2D detector responses and the corresponding predicted 2D detector responses minimizes a scoring function; and d. assigning the new values of treatment beam layer parameters and/or beam model parameters obtained after minimizing the scoring function as the delivered treatment beam layer parameters and/or delivered beam model parameters;

and wherein the step of computing for the one or more delivered treatment beam layers the delivered layer particle fluence through the object being based on the delivered treatment beam layer parameters and said delivered beam model parameters.

18. A method according to claim 16, wherein the method further comprises:

importing the planned 3D dose distribution in the object as calculated by an external treatment planning system;

comparing the planned 3D dose distribution with the delivered 3D dose; and reporting a set of parameters resulting from said comparison.

19. The device according to claim 1, wherein the device is configured to receive synchronization signals from a particle radiation apparatus for synchronizing the 2D detector device with the treatment beam delivery

* * * * *

UNITED STATES PATENT AND TRADEMARK OFFICE
CERTIFICATE OF CORRECTION

PATENT NO.       : 8,716,663 B2                                                                     Page 1 of 1
APPLICATION NO.  : 12/991372
DATED            : May 6, 2014
INVENTOR(S)      : Brusasco et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 559 days.

Signed and Sealed this
Twenty-ninth Day of September, 2015

Michelle K. Lee
*Director of the United States Patent and Trademark Office*